United States Patent
Braun (10) Patent No.: US 6,906,041 B2
(45) Date of Patent: Jun. 14, 2005

(54) TREATMENT OF IMMUNE DISEASES

(75) Inventor: Serge Braun, Dorlisheim (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/788,552

(22) Filed: Feb. 21, 2001

(65) Prior Publication Data

US 2002/0076399 A1 Jun. 20, 2002

Related U.S. Application Data

(60) Provisional application No. 60/246,089, filed on Nov. 7, 2000.

(30) Foreign Application Priority Data

Feb. 23, 2000 (EP) .............................................. 00440053

(51) Int. Cl.[7] ...................... A61K 48/00; C07H 21/0204
(52) U.S. Cl. ...................... 514/44; 536/23.1; 536/23.52
(58) Field of Search ........................ 514/44; 435/320.1; 424/43.1; 536/23.52

(56) References Cited

U.S. PATENT DOCUMENTS 5,580,859 A * 12/1996 Felgner et al. ................. 514/44
6,359,054 B1 * 3/2002 Lemieux et al. ............. 524/505

OTHER PUBLICATIONS

Youssef et al. The Journal of Immunology 161:3870–3879, 1998.*
Hernberg et al., Lyphocytes subsets as prognostic markers for cancer patients receiving immunomodulative therapy. 1999. Medical Oncology, vol. 16, pp. 145–153*
Martino et al., Cytokine therapy in immune–mediated demyelinating diseases of the central nervous systems a novel gene therapy approach 2000 Jouranl of Neuroimmunology, vol. 107, pp. 184–190.*
Crystal, Transfer of Genes to Humans: Early Lessons and Obstacles to Success, Oct. 20, 1995. Science vol. 270 pp. 404–409.*
Anderson Human gene therapy Apr. 30, 1998 vol. 392 Nature pp. 25–30.*
Triantaphyllopoulos et al. Cloning and expression of murine IFNB and a TNF antagonist for gene therapy of experimental allergic encephalomtelitis pp. 253–263 1998.*
Ludovic et al. Cytokine gene therapy in experimental allergic encephalomyelitis by injection of plasmid DNA–Cationic liposome complex into the central nervous system1 pp. 5181–5187 1998.*
Triantaphyllopoulos et al. Amelioration of collagen–induced arthritis and suppression of interferon–y, interleukin–13 and tumor necrosis factor a production by interferon–B gene therapy pp. 90–99 1999.*
Deonarain Ligand–targeted receptor–mediated vectors for gene delivery pp 53–69 1998.*
Verma et al. Gene therapy promises, problems and prospects pp. 239–242 vol. 389 1997.*

* cited by examiner

Primary Examiner—Ram R. Shukla
(74) Attorney, Agent, or Firm—Burns, Doane, Swecker & Mathis, L.L.P.

(57) ABSTRACT

The invention concerns the use of a nucleic acid capable of expressing beta-interferon for the preparation of a pharmaceutical composition for the treatment of an immune disease.

9 Claims, 5 Drawing Sheets

TREATMENT OF IMMUNE DISEASES

This application claims the benefit of Provisional Application No. 60/246,089, filed Nov. 07, 2000.

The present invention relates generally to the field of treatment of immune diseases in mammals, and more specially to the use of a nucleic acid capable of expressing beta-interferon for the preparation of a pharmaceutical composition for administration to a patient suffering from an immune disease.

Immune diseases widely concern affections of the immune system and/or its functions. They encompass for example allergic diseases (such as asthma, rhinitis, dermatitis), immune insufficiencies, inflammations (including acute or chronic inflammation, delayed-type hypersensitivity reactions) demyelinating disease associated with a humoral and/or cellular immune response and autoimmune diseases.

Autoimmunization relates to an immune reaction (either by production of antibodies, or of immunocompetent cells) specifically developed by the body against antigens of one's body own tissues. Autoimmune diseases are the consequence of this inappropriate autoimmunization developed against antigens normally present in the affected patient. Examples of autoimmune diseases include either cell-mediated diseases such as for example multiple sclerosis, rheumatoid arthritis, systemic lupus erythematous, or antibody-mediated diseases such as for example insulin dependent diabetes mellitus or myasthenia gravis (for general review, see "Fundamental immunology" $2^{nd}$ edition, William E. Paul Ed., Raven Press, New York (1989)).

One example of autoimmune diseases is multiple sclerosis. Multiple sclerosis is the major disabling neurological illness of young adults. It is an acquired primary demyelinating disease of the central nervous system (CNS) wherein myelin is the target of cellular autoimmune inflammatory process, leading to impaired nerve conduction (for a review, see e.g. Thompson 1996, Clin. Immunother. 5, 1–11). Clinical manifestations are variable, but are usually characterized by an initial relapsing-remitting course, with acute exacerbation followed by periods of clinical stability. Over time, a steady deterioration in neurological functions takes place as the disease evolves into a chronic progressive phase. This deterioration is responsible for disabling complications and side-effects, which greatly affect quality of life and increases mortality risk of affected patients.

Since multiple sclerosis is a T-cell-mediated autoimmune disease, several groups proposed clinical treatments based on the use of various immunomodulatory polypeptides. Actually, recent investigations have centered on the development of efficient methods using recombinant human beta-interferon as a therapeutic drug and provided a standard treatment of complications and side-effect disorders associated with multiple sclerosis, both related to the time-course and the intensity of the symptoms (for a review, see, e.g. Arnason, 1999, Biomed & Pharmacother. 53, 344–350).

Beta-interferon (INF-β) is a naturally-occurring glycoprotein (MW 22 KDa) comprising 166 amino acid residues associated with 21 amino acids responsible for secretion (see e.g. U.S. Pat. No. 4,738,931) which is primarily synthesized by diploid fibroblast cells and in lesser amounts by lymphoblastoid cells (for example upon microorganism/immune cell interaction). This protein plays important roles in the organism du to its plethora of biological effects. INF-β shows antiviral properties, inhibits cell proliferation, and modulates cytokine production (for a review see, e.g., Gresser I, 1997, J. Leukoc. Biol., 61, 567–774). Its nucleic acid and amino acid sequences have been first described in 1980 by Houghton et al., (1980, Nucleic Acids Research, 8, 2885–2894 and Tanigushi et al., (1980, Gene, 10, 11–15. Moreover, efficient recombinant methods for the production of recombinant beta-interferon have been developed in bacterial cells or in Chinese Hamster Ovary cells (Sburlati et al., 1998, Biotechnol Prog, 14, 189–192).

In 1993, the Food and Drug US Administration approved Betaseron™ for the treatment of multiple sclerosis. Two other similar treatments, Avonex™ (β-INF-1a) and Rebif™ (β-INF-1a), are now commercially available. These treatments consist in administering recombinant beta-interferon, either subcutaneously (the dosage is usually 0.25 mg ($8 \times 10^6$ IU) of recombinant β-INF-1b injected every day) or intramuscularly ($6 \times 10^6$ IU β-INF-1a injected weekly). They are mostly indicated for the treatment of ambulatory patients with relapsing-remitting multiple sclerosis and are still under evaluation for chronic-progressive patients (European Study Group published in 1998, Lancet, 352, 1491–1497). In relapsing-remitting multiple sclerosis, said administration of recombinant β-INF reduces the frequency and intensity of clinical exacerbations and delays the progression of disability, as well as disease activity (reviewed by Rudick et al., 1997, New England Journal of Medicine, 337, 1604–1611).

However, administration of recombinant interferon protein into mammals has been shown to cause undesirable systemic side-effects such as for example erythematous reactions at the injection-site or flu-like symptoms. Although these side-effects can generally be managed during the first few months of treatment, they are greatly restrictive in terms of dose which might be administered. Moreover, up to a third of patients receiving beta-interferon protein develop neutralizing antibodies to said protein, which may interfere with efficacy of the treatment. Additionally, pharmacokinetic studies on Betaferon™ published by the European Agency for the Evaluation of Medicinal Products, indicates that no level of beta-interferon was detectable in the blood of patients treated with a protein dose of $8 \times 10^6$ IU. The same has been evaluated using double dose, however only 40IU/ml were detected in the patient's blood for the first 8 hours post-injection and then dropped to an undetectable level (Rebif®, Product Monograph, Serono).

Although effectiveness of the exogenous recombinant beta-interferon supply to the patient has been supported, said protein-based treatment still requires that recombinant beta-interferon is repeatedly administered every 48 hours throughout the lifetime of the patient. This repetitive treatment can therefore increase the risk of developing immunity specifically directed against the beta-interferon and which would make the clinical status of the affected patient worse.

Accordingly, the prior art is deficient in providing a satisfactory treatment of immune diseases, especially autoimmune diseases such as for example multiple sclerosis. Thus the technical problem underlying the present invention is to provide means for a satisfactory treatment of such immune diseases.

Since the discovery that skeletal muscle can be transfected in vivo by transmuscular injection of plasmid DNA, this organ system has attracted considerable attention as a potential source of secreted therapeutic proteins. However, the efficiency of this method of transfection is still low, even with the induction of muscle degeneration and regeneration through injection of myotoxic substances prior the injection of DNA. Accordingly, most studies so far have shown that expression is not high enough to increase the blood levels of circulating proteins, especially in case where this level should be high enough for permitting an improvement of the health. Actually, this plasmid DNA based gene therapy is still limited to vaccination applications (MacGregor et al. 1998, J. Infec. Dis. 178, 92–100; Wang et al., 1998, Science, 282, 476–480).

It was now surprisingly found that nucleic acid (DNA or RNA) capable of expressing beta-interferon (INF-β) when injected into mammal suffering from an immune disease, preferably those provoking demyelination of the central nervous system, and more specifically autoimmune diseases (e.g. multiple sclerosis, . . . ), can induce an unexpected improvement of the health of the treated mammal when compared to untreated mammal. This allows for the treatment of said immune diseases, while avoiding the use of recombinant polypeptide.

Accordingly, the present invention relates to the use of a nucleic acid capable of expressing beta-interferon for the preparation of a pharmaceutical composition for the treatment of an immune disease.

Thus, the present invention fulfills a longstanding need and desire in the art. More particularly, it provides a satisfactory treatment method providing an acceptable level of beta-interferon in treated patients and being compatible with the quality of life of the patients.

In the context of the present invention, the term "immune disease" encompasses any disease which is associated with the development of an immune reaction, either a cellular or a humoral immune reaction, or both. Those terminologies are widely used in the field of immunology and are, thus, well known in the art. Examples of immune diseases are inflammation, allergy and autoimmune diseases.

In one preferred embodiment, said immune disease is a demyelinating disease characterized by a demyelinating process of the central nervous system, such as for example multiple sclerosis, sub-acute sclerosing panencephalomyelitis (SSPE), metachromatic leukodystrophy, inflammatory demyelinating polyradiculoneuropathy, Pelizaeus-Merzbacher disease, and Guillain-Barré syndrome (see Choudhary et al., 1995, J. Neurol. 242 252–253; Créange et al. 1998, The Lancet 352 368). Demyelination is a pathological end-point that is common to all of these diseases, while the cellular and molecular mechanisms originally responsible for this pathology are very different. These range from genetic defects that affect lipid metabolism in the leukodystrophies, cytopathic effects of viral infection in SSPE to the action of immunological effector mechanisms in multiple sclerosis and the viral encephalopathies. Irrespective of said initial cause of myelin degradation, these disorders are associated with central nervous system inflammation, with local activation of microglia, recruitment of macrophages or the intrathecal synthesis of immunoglobulin. Similarly, it has been shown that there are interrelationships between the immune response in the central nervous system and the pathogenesis of diseases such as, for example, Alzheimer's disease or HIV encephalopathy (Bradl and Linington, 1996, Brain Pathol, 6, 303–11).

In a still more preferred embodiment, said immune disease is an autoimmune disease. "Autoimmune disease" broadly refers to an immune disease wherein the immune response is developed against antigens normally present in the affected patient. It can be an organ specific autoimmune disease (the immune response is for example specifically directed against the endocrine system, the hematopoietic system, the skin, the cardiopulmonary system, the neuromuscular system, the central nervous system, etc) or a systemic autoimmune disease (for example, Systemic lupus erythematosous, Rheumatoid arthritis, polymyositis, etc). In a particularly preferred embodiment, the autoimmune disease is multiple sclerosis.

In accordance with the invention, "treatment of an immune disease" means that at least the complications and side-effects disorders associated with said immune disease are reduced in the treated affected mammal compared to those observed in the untreated affected mammals. "Affected mammal" designates a mammal which presents symptoms of the considered immune disease, and preferably those which have been clearly diagnosed by any useful and available method. "Complications and side-effect disorders associated with said immune disease are reduced" can be widely understood and preferably means that application of said treatment to an affected mammal reduces the frequency and intensity of clinical exacerbations and delays the progression of disability, as well as disease activity (see, e.g., Rudick et al., 1997, New England Journal of Medicine, 337, 1604–1611). These reductions can be easily measured by a person skilled in the art, e.g. a clinician using commonly known and used methods.

"Nucleic acid capable of expressing beta-interferon" designates a nucleic acid which comprises a polynucleotide sequence encoding a beta-interferon polypeptide which is operably linked to a transcriptional control sequence so as to ensure transcription in the target cells. According to the present invention, said "nucleic acid" can be a fragment or a portion of a polynucleotide sequence, without size limitation, which may be either linear or circular, natural or synthetic, modified or not (see U.S.Pat. No. 5,525,711, U.S. Pat. No. 4,711,955, U.S. Pat. No. 5,792,608 or EP 302175 for modification examples). Depending on the considered sequence, it may be, inter alia, a genomic DNA, a cDNA, a mRNA or a synthetic DNA. According to the invention, said nucleic acid can be either naked or non-naked. "Naked" means that said nucleic acid, irrespective of its nature (DNA or RNA), its size, its form (for example single/double stranded, circular/linear), is defined as being free from association with transfection-facilitating viral particles, liposomal formulations, charged lipids, peptides or polymers and precipitating agents (Wolff et al., 1990, Science 247, 1465–1468; EP 465529). On the opposite, "non-naked" means that said nucleic acid may be associated (i) with viral polypeptides forming what is usually called a virus (adenovirus, retrovirus, poxvirus, etc . . . ) or forming a complex where the nucleic acid while being associated with is not included into a viral element such as a viral capsid (see, e.g., U.S. Pat. No. 5,928,944 and WO 9521259), (ii) with any component which can participate in the transfer and/or uptake of the nucleic acid into the cells. According to the invention, the nucleic acid sequence can be homologous or heterologous to the host cells. Preferably, the nucleic acid is in the form of plasmid DNA and the polynucleotide is a naked plasmid DNA. A wide range of plasmids is commercially available and well known by one skilled in the art. These available plasmids are easily modified by standard molecular biology techniques (e.g., Sambrook et al, 1989, Molecular cloning, A Laboratory Manual, Cold Spring Harbor Laboratory Press, Cold Spring Harbor, N.Y.). Plasmids derived from pBR322 (Gibco BRL), pUC (Gibco BRL), pBluescript (Stratagene), pREP4, pCEP4 (Invitrogen) and also pPoly (Lathe et al., 1987, Gene 57, 193–201) are illustrative of these modifications.

The term "a polynucleotide sequence encoding a beta-interferon potypeptide" in the context of the present invention relates to any polynucleotide sequence encoding a beta-interferon polypeptide, in particular a polypeptide having the biological activities of beta-interferon such as antiviral or immunomodulatoring properties (see, e.g., Arnason B., 1999, supra).

Polynucleotide sequences encoding a beta-interferon polypeptide are readily available, e.g., through a number of computer data bases, for example GenBank, EMBL and Swiss-Prot. Using this information, a polynucleotide (DNA or RNA) segment encoding the desired polypeptide may be chemically synthetized, or alternatively, such a DNA segment may be obtained using routine procedures in the art, e.g. PCR amplification using specific primer sequences. Examples of such nucleic acid sequences available in the GenBank database have the Accession Numbers M15477, M15478 or M15479 for bovine INF-β; S41178 or M86762 for pig INF-β; X14029 or X14455 for mouse INF-β; M14546 for horse INF-β; D87919 for rat INF-β; K03196, M25460, X04430, M16656 or E00038 for human INF-β. In the scope of the present invention also sequences can be used which encode analogues of the beta-interferon, examples for such sequence are the sequence available under GenBank Accession Numbers E00017, E00352, E00353 or E00354. INF-β encoding sequences are also disclosed in Houghton et al., 1980, Nucleic Acids Research, 8, 2885–2894, Taniguchi et al., 1980, Gene, 10, 11–15 and U.S. Pat. No. 4,738,931. Preferably, the nucleic acid used in the present invention encodes a beta-interferon protein having the amino acid sequence as set forth in SEQ ID NO:1 or SEQ ID NO:2. SEQ ID NO:1 contains a secretory 21 amino acid signal sequence that facilitates secretion of the synthetized protein from the expressing cells; SEQ ID NO:2 shows the beta-interferon protein not including said secretory signal sequence. A nucleic acid sequence which encodes a beta-interferon protein having its native signal sequence is preferred. The native signal sequence may however be replaced with heterologous signal sequences (using routine genetic manipulation techniques; see Nabel et al., 1993, Nature, 362, 844). "Beta-interferon or INF-β" according to the present invention preferably designates a polypeptide having the amino acid sequence as set forth in SEQ ID NO:1. However minor amino acid variations are acceptable in the INF-β polypeptide sequence which do not affect the INF-β properties. Accordingly, and with regard to the degeneracy of the genetic code, the skilled man can easily adapt the polynucleotide sequence encoding beta-interferon with respect to these minor changes. These specific embodiments are encompassed by the invention. According to a preferred embodiment, the nucleic acid sequence used in the invention encodes human beta-interferon and in a particularly preferred embodiment it comprises the nucleotide sequence as set forth in SEQ ID NO:3 (human INF-β).

In accordance with the present invention, "operably linked to a transcriptional control sequence" means that the encoding polynucleotide sequence and the transcriptional control sequence are in a relationship permitting them to function in their intended manner. Thus, for example, a promoter operably linked to a polynucleotide sequence is ligated to it in such a way that expression of the beta-interferon is achieved under conditions which are compatible with the transcriptional activity of the promoter. These conditions are widely used in the technical field of the invention. "Transcriptional control sequence" designates the polynucleotide sequences which control, e.g., the initiation of the transcription, the selection of the start position, which regulate the transcription level (enhancement or inhibition), which determine the type of polymerase directing the polymerisation of the transcribed mRNA, which control the transcription rate, the termination of said transcription, the site of said termination, . . . These sequences are widely analyzed, used and reported in the literature and can be readily obtained or adapted by those skilled in the art.

In preferred embodiment, the transcriptional control sequence comprises a promoter element. Preferably, one would use a high expression promoter. Said promoter may be for example selected from the group consisting of viral promoters and muscle specific promoters, or a combination thereof. Examples of such viral promoters are the SV40 early and late promoters, the adenovirus major late promoter, the Rous Sarcoma Virus (RSV) promoter, the Cytomegalovirus (CMV) immediate-early promoter, the herpes simplex virus (HSV) promoter, the MPSV promoter, the 7.5 k promoter, the vaccinia promoter and the Major-intermediate-early (MIE)promoter. Examples of muscle specific promoters are the smooth muscle 22 (SM22) promoter, the myosin light chain promoter, the myosin heavy chain promoter, the skeletal alpha-actin promoter and the dystrophin promoter. The Cytomegalovirus (CMV) immediate-early promoter is however preferred. The natural promoter of the beta-interferon encoding sequence might also be used (U.S. Pat. No. 4,738,931). The polynucleotide sequence of the promoter can be a naturally occurring promoter sequence isolated from biological nucleic acid material or chemically synthesized. The promoter sequence can also be artificially constructed by assembling elements previously screened for transcriptional activity leading to potencies which can exceed those of naturally occurring ones (Li et al., 1999, Nature Biotech., 17, 241–245). The expression cassette (coding sequence and promoter can be constructed using routine cloning techniques known to persons skilled in the art (for example, see Sambrook et al., 1989, supra). In still another aspect of the invention, the transcriptional control sequence further comprises at least one enhancer element. The term "enhancer" refers to a regulatory element which activates transcription in a position and orientation independent way. Several enhancer elements have been identified to date in many genes. For example, the enhancer element may be a myosin light chain enhancer. More preferably, the enhancer used in the expression cassette of the present invention is of vertebrate origin, more preferably of mammalian origin. The rat myosin light chain ⅓ enhancer (Donoghue et al., 1988, Gene & Dev., 2, 1779–1790) is especially useful. The enhancer element is operably linked to the promoter, may be localized either upstream or downstream of said promoter and may be used in either orientation. According to a preferred embodiment, the transcriptional control sequence comprises several enhancer sequences, the sequences of which are identical or selected independently of one another. Preferably, the transcriptional control sequence further comprises at least one sequence ensuring the polyadenylation of the transcribed RNA molecules. Such a sequence may be selected from the group consisting of the bGH (bovine growth hormone) polyadenylation signal (EP 173552), the SV40 polyadenylation signal and the globine polyadenylation signal, and is generally located at the 3'-end of the sequence encoding beta-interferon.

In a preferred embodiment the nucleic acid used in the present invention can further comprise a polynucleotide sequence encoding at least one polypeptide of interest which is distinct from beta-interferon, said polypeptide of interest being co-expressed with beta-interferon in the target cell. Alternatively, it is also possible that the second polynucleotide sequence is part of a second nucleic acid which is administered simultaneously with the beta-interferon encoding sequence. Said polypeptide of interest may be, e.g., a selectable marker such as an antibiotic resistance polypeptide, an immunomodulatory polypeptide (for example IL4, IL6, IL6, IL10 or TGF beta), a neurotrophic factor (for example NGF, neurotrophin, BDNF or cardiotrophin), a growth factor (e.g.,IGF-1), all or part of an antibody (for example an anti-idiotype antibody or an anti-TNF antibody), a hormone (for example LH, FSH or adrenocorticotrophin hormone), an anti-inflammatory polypeptide or a hybrid polypeptide thereof.

Furthermore the nucleic acid used in the present invention can further include at least one nucleotide sequence containing or expressing a targeting sequence, a transport sequence, a sequence involved in replication or integration, or a sequence encoding a selectable marker, for example for antibiotic resistance (ampicilin, phleomycin, chloramphenicol, . . . ), useful for selecting a cell in which said nucleotide sequence has been introduced. Examples for such sequences have been reported in the literature and can be readily obtained by those skilled in the art. The nucleic acid can also be modified in order to be stabilized with specific components such as spermine.

In a preferred embodiment, the nucleic acid used in the present invention is DNA associated with a transfection-facilitating vehicle. "Transfection-facilitating vehicle" can, e.g., be selected from the group consisting of viral particles, cationic lipids, cationic polymers and polypeptides. Viral particles involve especially adeno- and retroviral particles (a viral particle associated with the nucleic acid is called a viral vector). Viruses have developed diverse and highly sophisticated mechanisms to achieve delivery of their genome to cells and, consequently, have been used in many gene delivery applications in vaccination or gene therapy applied to humans.

Other "transfection-facilitating vehicles" are non-viral delivery systems which are, e.g., based on receptor-mediated mechanisms (Perales et al., Eur. J. Biochem. 226 (1994), 255–266; Wagner et al., Advanced Drug Delivery Reviews 14 (1994), 113–135), on polymer-mediated transfection such as polyamidoamine (Haensler and Szoka, Bioconjugate Chem. 4 (1993), 372–379), dendritic polymer (WO 95/24221), polyethylene imine or polypropylene imine (WO 96/02655), polylysine (U.S. Pat. No. 5,595,897 or FR 2 719 316) or on lipid-mediated transfection (Feigner et al., Nature 337 (1989), 387–388) such as DOTMA (Feigner et al., Proc. Natl. Acad. Sci. USA 84 (1987), 7413–7417), DOGS or Transfectam™ (Behr et al., Proc. Natl. Acad. Sci. USA 86 (1989), 6982–6986), DMRIE or DORIE (Felgner et al., Methods 5 (1993), 67–75), DC-CHOL (Gao and Huang, BBRC 179 (1991), 280–285), DOTAP™ (McLachlan et al., Gene Therapy 2 (1995), 674–622) or Lipofectamine™ (see Rolland, 1998, 15, 143–198 for a review). In a preferred embodiment, the "transfection-facilitating vehicle" of the invention comprises at least one substance which is a cationic substance, and in a still more preferred embodiment said cationic substance is a cationic lipid or a cationic polymer. Advantageously, said cationic lipid is a cationic lipid as disclosed in WO 98/34910.

The pharmaceutical composition described above can be administered by any suitable route. Administration into vertebrate target tissues, and more specifically into the muscle, can be performed by different delivery routes (systemic delivery and targeted delivery). According to the present invention, the pharmaceutical composition is preferably administered into skeletal muscle, however administration can also occur in other tissues of the vertebrate body including those of non skeletal muscle, skin, brain, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor . . . The beta-interferon can thus be excreted in body fluids (eg. blood) allowing its delivery to the patient's organs. Similarly, the nucleic acid can be associated with targeting molecules which are capable to direct its uptake into targeted cells. Gene therapy literature provides many mechanisms for efficient and targeted delivery and expression of genetic information within the cells of a living organism. Administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol routes. Injection, and specifically intramuscular injection, is preferred.

The pharmaceutical composition can be designed or used for repeated administrations to the patient without major risk of the administered pharmaceutical composition to induce a significant immune reaction. Administration may be by single or repeated dose, once or several times after a certain period of time. Repeated administration allows a reduction in the dose of nucleic acid administered at a single time. The route of administration and the appropriate dose vary in function of several parameters, for example the individual patient, the side effects of the disease, or the albumin level before treatment.

Preferably, the concentration of the nucleic acid in the pharmaceutical composition is from about 0.1 µg/ml to about 20 mg/ml.

The active dose, or the amount of nucleic acid which should be injected for obtaining satisfactory beta-interferon, is preferably from about 1 µg to 1 g, more preferably from about 1 mg to 1 g, most preferably from about 1 mg to 100 mg. Said active dose can be administered in a unique administration or in multiple ones distributed over one or more days. Preferably, the maximum single dose is 10 mg of DNA administered. The separate administrations can be performed by different delivery routes (systemic delivery and targeted delivery, or targeted deliveries for example). In a preferred embodiment, each delivery should be done into the same target tissue and most preferably by injection.

The administered volume preferably varies from about 10 µl to 500 ml, most preferably from about 100 µl to 100 ml. The administered volume can be adapted depending on the administration route, the treated patient and the patient's weight.

The present invention further relates to a kit comprising a nucleic acid capable of expressing beta-interferon and a delivery tool. Preferably, the nucleic acid is in solution in a pharmaceutically acceptable carrier. In a preferred embodiment, the nucleic acid is a nucleic acid as described herein above in connection with the use according to the invention. The kit is intended for gene transfer, especially for the treatment of the human or animal body, and in particular for the treatment of an immune disease. With respect to preferred embodiments of the kit of the present invention, the same holds true as already set forth above in connection with the use according to the present invention.

The present invention also relates to a method for treating an immune disease in a mammal which comprises administering to said mammal an effective amount of a nucleic acid encoding beta-interferon operably linked to a promoter to result in expression of the protein when delivered to a tissue of the mammal. The expression of the beta-interferon protein results in an improvement of the clinical status of the treated mammal. The method of the invention may be used to treat a mammal suffering from an immune disease, especially from an autoimmune disease and more particularly from multiple sclerosis.

As used herein, the term "effective amount" means a sufficient amount of a nucleic acid delivered to the cells of the treated mammal to produce an adequate level of beta-interferon, i.e. a level capable of inducing amelioration of the health of the treated mammal. Thus, the important aspect is the level of protein expressed. Accordingly, one can use multiple transcripts or one can have the gene encoding beta-interferon under the control of a promoter that will result in high levels of expression. In an alternative embodiment, the gene can be under the control of a factor that results in extremely high levels of expression, e.g., tat and the corresponding tar element. With respect to preferred embodiments of the method according to the present invention, the same holds true as already set forth above in connection with the use according to the present invention.

In the course of the in vivo treatment according to the present invention, in order to improve the transfection rate of the administered nucleic acid, the patient may undergo a macrophage depletion treatment prior to administration of the pharmaceutical composition described above. Such a technique is described in the literature (refer particularly to Van Rooijen et al., 1997, TibTech, 15, 178–184). The patient can also be pre-treated with prednisolone or an equivalent thereof.

In a preferred embodiment, the method according to the present invention involves administration into a fluid vessel, such as for example a blood vessel or a lymph vessel, and can be advantageously improved by combining injection in an afferent and/or efferent fluid vessel with increases of permeability of said vessel. In a particularly preferred embodiment, said increases is obtained by increasing hydrostatic pressure (i.e. by obstructing outflow and/or inflow), osmotic pressure (with hypertonic solution) and/or by introducing a biologically active molecule (e.g. histamine into administered composition) (see, e.g., WO 98/58542).

The invention also relates to a pharmaceutical composition containing a nucleic acid capable of expressing beta-interferon and a pharmaceutically acceptable carrier.

"Pharmaceutically acceptable carrier" allows use of the pharmaceutical composition in a method for the therapeutic treatment of humans or animals. In this particular case, the carrier can be a pharmaceutically suitable injectable carrier or diluent (for examples, see Remington's Pharmaceutical Sciences, 16$^{th}$ ed. 1980, Mack Publishing Co). Such carrier or diluent is pharmaceutically acceptable, i.e. is non toxic to a recipient at the dosage and concentration employed. It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g. Tris-HCl, acetate, phosphate), emulsifiers, solubilizers or adjuvants. The pH of the pharmaceutical preparation is suitably adjusted and buffered in order to be useful in in vivo applications. It may be prepared either as a liquid solution or as a solid form (e.g. lyophilized) which can be suspended in a solution prior to administration. Representative examples of carriers or diluents for injectable formulation include water, isotonic saline solutions which are preferably buffered at a physiological pH (such as phosphate buffered saline or Tris buffered saline), mannitol, dextrose, glycerol and ethanol, as well as polypeptides or protein such as human serum albumin. For example, such formulations comprise the pharmaceutical composition prepared according to the use of the present invention in 10 mg/ml mannitol, 1 mg/ml HSA, 20 mM Tris pH 7.2 and 150 mM NaCl.

In a further preferred embodiment the invention pertains to a pharmaceutical composition comprising at least one nucleic acid capable of expressing beta-interferon described above and at least one adjuvant capable of improving the transfection capacity of said nucleic acid (naked or non-naked), or gene expression in the cell. Such an adjuvant can be selected from the group consisting of chloroquine, protic compounds such as propylene glycol, polyethylene glycol, glycerol, ethanol, 1-methyl L-2-pyrrolidone or derivatives thereof, aprotic compounds such as dimethylsulfoxide (DMSO), diethylsulfoxide, di-n-propylsulfoxide, dimethylsulfone, sulfolane, dimethyl-formamide, dimethylacetamide, tetramethylurea, acetonitrile or derivatives. The composition may also advantageously comprise a source of a cytokine which is incorporated in the form of a polypeptide or as a polynucleotide encoding the cytokine. Preferably, said cytokine is interleukin 10 (IL-10)(EP-A-967 289). The therapeutic composition can further comprise a nuclease inhibitor such as actine G, or specific magnesium or lithium concentrations.

The invention further concerns a host cell transformed with a nucleic acid capable of expressing beta-interferon. Said host cell is preferably a mammalian cell, and more preferably a human muscular cell. This cell can originate from various tissues including those of muscle, skin, nose, lung, liver, spleen, bone marrow, thymus, heart, lymph, bone, cartilage, pancreas, kidney, gall bladder, stomach, intestine, testis, ovary, uterus, rectum, nervous system, eye, gland, connective tissue, blood, tumor etc.

According to the invention, "transformed" means either transfection or infection, and more broadly designate any transferring step resulting in introduction of said nucleic acid into said host cell. Said transferring step can be implemented by any of a wide variety of ways, including a method selected from the group consisting of adenoviral infection, transfection with nucleic acid coated particles such as lipoplexes (cationic lipid/nucleic acid complexes) or polyplexes (cationic polymer/nucleic acid complexes) or the like, calcium phosphate transfection of plasmid, transfection with naked nucleic acid, electroporation method or any combination thereof. However, the particular method for introducing the foreign nucleic acid sequence is not crucial to the invention.

Moreover according to a specific embodiment, said transformed host cell is a human muscular cell which is further encapsulated. Cell encapsulation methodology has been previously described which allows transplantation of encapsulated cells in treatment of Parkinson's disease (Tresco et al., 1992, ASAIO J., 38, 17–23) or amyotrophic lateral sclerosis (Aebischer et al., 1996, Hum. Gene Ther., 7, 851–860). According to said specific embodiment, transformed cells are encapsulated by compounds which form a microporous membrane, and said encapsulated cells can further be implanted in vivo. Capsules, for example approximately 1 cm in length containing the cells of interest may be prepared employing a hollow microporous membrane fabricated from poly-ether-sulfone (PES) (Akzo Nobel Faser AG, Wuppertal, Germany; Déglon et al, 1996, Hum. Gene Ther., 7, 2135–2146). This membrane has a molecular weight cutoff greater than 1,000,000 Da, which permits the free passage of proteins and nutrients between the capsule interior and exterior, while preventing the contact of transplanted cells with host cells. The entrapped cells may be implanted by intradermal, subdermal, intravenous, intramuscular, intranasal, intracerebral, intratracheal, intraarterial, intraperitoneal, intravesical, intrapleural, intracoronary or intratumoral ways. In case where said transformed host cell is a myoblast, it can migrate from the site of injection to muscles where expression of beta-interferon can occur.

While the present invention has been described with reference to preferred embodiments and specific examples, one of the ordinary skill after reading the foregoing specification will be able to effect various changes, substitutions of equivalents, and other alterations to the processes and produced cells set forth herein. It is therefore intended that the protection claimed hereon be limited only by the definition contained in the appended claims and equivalents thereof.

These and other embodiments are disclosed or are obvious from and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet. Further databases and Internet addresses are known to the person skilled in the art. An overview of patent information in biotechnology and a survey of relevant sources of patent information useful for retrospective searching and for current awareness is given in Berks, TIBTECH 12 (1994), 352–364.

The invention has been described in an illustrative manner, and it is to be understood that the terminology which has been used is intended to be in the nature of words of description rather than of limitation. Obviously, many modifications and variations of the present invention are possible in light of the above teachings. It is therefore to be understood that within the scope of the appended claims, the invention may be practiced different from what is specifically described herein.

All of the above cited disclosures of patents, publications and database entries are specifically incorporated herein by reference in their entirety to the same extent as if each such individual patent, publication or entry were specifically and individually indicated to be incorporated by reference.

LEGENDS OF THE FIGURES

FIG. 2: detection of human IFN-β in the blood of mice injected with pTG13102. Bars are man values +/ −sem of 3 determinations (3 mice per group). White bars: after injection of plasmid prepared in NaCl 0.9%. Black bars: after administration of plasmid with adjuvants described in the text.

EXAMPLES

Example 1

Construction and Validation of a Plasmid Encoding Human INF-β

The backbone plasmid pTG11022 is described in Braun et al., 1999, FEBS Letters, 454, 277–282. It is an *E.coli* plasmid, based on the ColE1 origin of replication. It contains the kanamycin-resistance gene, the mouse HMGCR intron and the human cytomegalovirus IE1 promoter (from pCEP4, InVitrogen, Abingdon, UK).

The human INF-β cDNA was obtained by PCR amplification of human DNA extracted from the human T-cell line CEM A 3.01 (NIH Research and Reference Reagent Program, # 166), and sequenced. It was verified that its amino acid sequence is similar to the published sequence (Tanigushi et al, 1980, supra). The expression cassette was taken from an intermediate plasmid M13TG2449. The backbone plasmid pTG11022 was cut with Pvull. M13TG2449 was cut with Smal and EcoRV. The purified 605 bp INF-β insert was ligated to the opened pTG11022, giving rise to the final plasmid designated pTG13102. Orientation was checked with Pstl digest and agarose 1% gel electrophoresis.

Plasmid pTG13102 was amplified in *E. coli* strain MC1061 by overnight culture in LB medium and purified by double cesium chloride gradient centrifugation after alkaline lysis according to standard techniques (see Sambrook et al., 1989, $2^{nd}$ *Edition, Cold Spring Harbor Laboratory,* Cold Spring Harbor N.Y.). Purified plasmid DNA was concentrated to 1 mg/ml in NaCl 0.9%+solution.

Validation in vitro

Human INF-β expression was measured in the culture supernatant of the mouse myoblast cell line C2C12 (ATCC CRL-1772) following calcium phosphate transfection with pTG13102. Calcium phosphate transfection was performed according to the standard protocol. INF-β release in the culture medium was measured on a regular basis up to 6 days following transfection with pTG13102.

Figure 1:
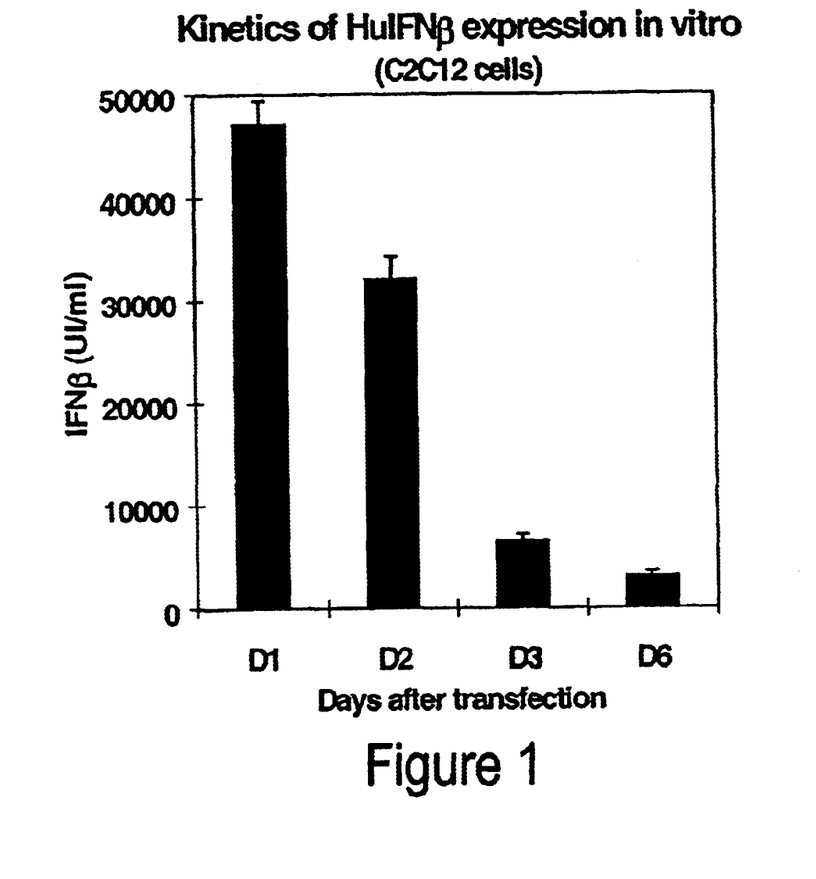
FIG. 1 shows the amount of human INF-β (Hu INF-β) found in the culture media of the transfected cells. Bars are mean values +/− standard error of the mean value (sem) of 4 determinations. D1, 2, 3, 6: Days after transfection.

For that purpose, 15 μg of pTG13102 plasmid were transfected in 6 well-plates seeded with $10^5$ C2C12 cells/ well cultured in Dulbecco's Modified eagle Medium (DMEM) containing 10% fetal calf serum. Four wells were transfected with pTG13102 and 2 wells with pTG11033 a pTG11022-based plasmid with a fire-fly luciferase expression cassette (plasmid used as negative control for INF-β). Culture media were collected and frozen for INF-β measurement, and they were replaced with fresh medium. The medium harvests were performed at day 0 (right before transfection; this corresponds to the control non-transfected cells), 24 hrs post-transfection, 48 hrs post-transfection (this corresponds to a 24hr-secretion period between day+1 and day+2, as the culture media were replaced at 24 hrs), 3 days post-transfection (24 hrs secretion period between day+2 and day+3) and 6 days post-transfection (3 day-secretion period between day+3 and day+6). Human INF-β content of the culture media was measured using a human INF-β detection ELISA kit (Fujirebio, Tokyo, Japan) and expressed as IU/ml (FIG. 1).

No human INF-β was found in the 2 supernatants (2 wells used) of pTG11033 (irrelevant plasmid used as control) transfected cells, or in the culture medium collected prior to transfection (at day 0).

Verification of the Biological Activity of the Human IFN-β Produced

The biological activity of the human INF-β was analyzed using a conventional Cytopathic Effect (CPE) Assay. The principle of the assay is based on the antiviral activity of interferons. Measurements are performed on serial dilutions of the collected culture media of plasmid-transfected C2C12 cultures. The dilutions are incubated with human amniotic WISH cells infected with Vesicular Stomatitis Virus (VSV). The VSV cytopathic effect leads to cell death which is assessed by microscopic evaluation. The amount of human INF-β is determined according to the dilution of the test sample which protects 50% of the cells from VSV-induced death (eg., a 10-fold dilution=10 IU/ml). Standard controls were human INF-β NIH and the human INF-β standard of the Fujirebio ELISA kit.

For that purpose, WISH cells were seeded in DMEM+ 10% FCS in 96-well plates ($5 \times 10^4$ cells/well). Cascade dilutions of standard human INF-β or of the C2C12 culture media to test were prepared in DMEM+10% FCS, and added to the WISH cells immediately after seeding (duplicate wells). Cells were then infected with VSV (M.O.I.=2, that is 2 viral infectious unit per cell). The cell viability was assessed 24 hrs after infection.

Table I shows the comparative ELISA/CPE INF-β titers of C2C12 samples. Supernatants of C2C12 cultures transfected with pTG13102 (pCMV-INF-β)

TABLE I

| Sample | As measured by ELISA | As measured by CPE |
|---|---|---|
| day 0 (negative control) | 0 | <1.5 |
| day 1 after transfection | 47324 | 63100 +/− 3000 |
| day 3 after transfection | 6404 | 8000 +/− 1610 |

Note: +/− is not SD but is related to the dilution factor used
IFN titers were equivalent between ELISA and CPE assays, indicating that the human INF-β pTG13102 plasmid allowed production of a biologically functional INF-β.

Expression of IFN-β after Intramuscular Injection of pTG13102 Plasmid (pCMV-human IFN-β) in Mice Plasmid pTG13102 was injected into 6–8 week-old C57Bl/10 and SCID mice (4×25 μg plasmid in the right and left tibialis and quadriceps muscles). Muscles were treated 3 days prior to plasmid administration with injection of 3 ng/25 μl of notexine in order to induce muscle regeneration (which follows the notexin-induced necrosis). pTG13102 was prepared in either NaCl 0.9% alone or in NaCl 0.9% added with 10 μg G-actin, 0.1 mM $MgCl_2$ and 10% DMSO final. Plasmid injection volume was 35 μl.

Sera were prepared from the mouse blood samples which were collected at various time points after plasmid injection. Control sera correspond to samples collected at day 0 before plasmid injection, or samples of mice non-injected with pTG13102.

Mice were sacrificed at various time points (7 and 14 days after plasmid injection) and the injected muscles were collected and frozen. The frozen muscles were grinded into PBS buffer (600 μl and 400 μl volume for tibialis and quadriceps respectively). The preparations were centrifuged and aliquotes of supernatants were used for huIFN-β measurement (using the Fujirebio ELISA kit).

Results shown in FIG. 2 indicate that detectable levels of human INF-β may be obtained following direct intramuscular injections of plasmid preparations.

Figure 2A:
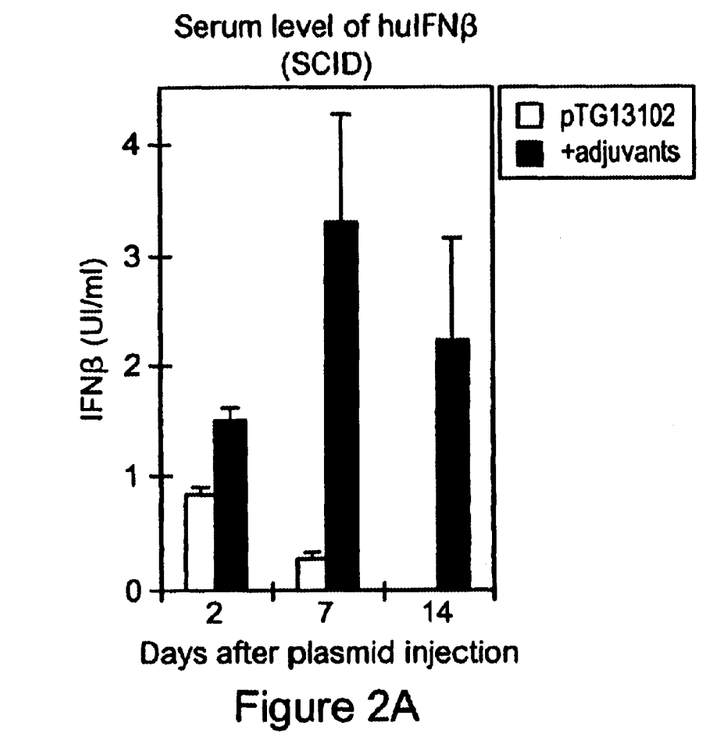
FIG. 2A: injections in SCID mice.
Figure 2B:
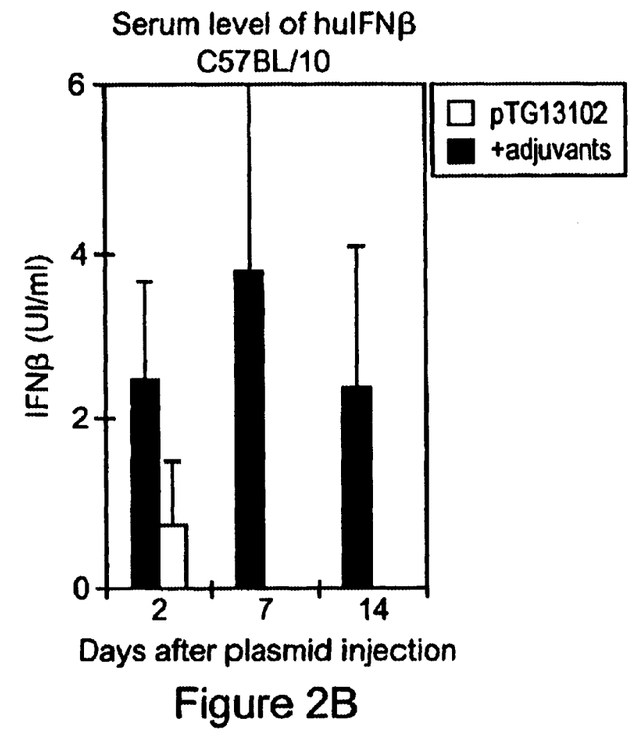
FIG. 2B: in immunocompetent C57B/10 mice.

As shown in FIG. 2, human INF-β was detected for at least 2 weeks in sera of both SCID (FIG. 2A) and C57BL/10 mice (FIG. 2B). Similar blood levels of human INF-β found in both SCID and immunocompetent C57BL/10 mice.

No human INF-β was detected neither in the blood of the control non-injected mice nor in blood samples of plasmid-injected mice collected at day 0.

Table II shows human INF-β levels found in the muscles and serum of each individual mouse.

| Mouse # (day post injection) | INJECTION | UI/muscle | | | | UI/ml serum | |
|---|---|---|---|---|---|---|---|
| | | Left TA | Right TA | Right Q | Left Q | Day 7 | Day 14 |
| SCID | | | | | | | |
| 1 | pTG13102 | 5 | 4 | 1.2 | | 0.3 | |
| 2 | pTG13102 | 1 | 2 | | | 0.15 | |
| 3 | pTG13102 | 8 | 1 | | | 0.35 | |
| (day 7) | mean | 4.67 | 2.33 | 1.20 | | 0.27 | |
| | sem | 2.03 | 0.88 | | | 0.06 | |
| 4 | pTG13102+adjuvants | 27 | 36 | 1.02 | | 2.3 | |
| 5 | pTG13102+adjuvants | 0 | 24 | | 3.9 | 3.4 | |
| 6 | pTG13102+adjuvants | 23 | 11 | | 1.2 | 1 | |
| (day 7) | mean | 16.67 | 23.67 | 1.02 | 2.55 | 2.23 | |
| | sem | 8.41 | 7.22 | | | 0.69 | |
| 7 | pTG13102+adjuvants | 6 | 36 | 1 | | 3.6 | 1.33 |
| 8 | pTG13102+adjuvants | 9 | 2 | | | 0.6 | 0.35 |
| 9 | pTG13102+adjuvants | 20 | 0 | 0 | 1.62 | 1.6 | 0.9 |
| (day 14) | mean | 11.67 | 12.67 | 0.50 | 1.62 | 1.93 | 0.86 |
| | sem | 4.26 | 11.68 | | | 0.88 | 0.28 |
| C57BL10 | | | | | | | |
| 13 | pTG13102 + adjuvants | 9 | 7 | | | 1.2 | |
| 14 | pTG13102 + adjuvants | 0 | 22 | | | 3.3 | |
| 15 | pTG13102 + adjuvants | 47 | 4 | | | 1.5 | |
| (day 7) | mean | 18.67 | 11.00 | | | 2.00 | |
| | sem | 14.40 | 5.57 | | | 0.66 | |

-continued

| Mouse # (day post injection) | INJECTION | UI/muscle | | | | UI/ml serum | |
|---|---|---|---|---|---|---|---|
| | | Left TA | Right TA | Right Q | Left Q | Day 7 | Day 14 |
| 16 | pTG13102 + adjuvants | 17 | 69 | 2.1 | | 15 | 5.7 |
| 17 | pTG13102 + adjuvants | 18 | 0 | | | 1.5 | 1.4 |
| 18 | pTG13102 + adjuvants | 0 | 1 | | | 0.3 | 0 |
| (day 14) | mean | 11.67 | 23.33 | 2.10 | | 5.60 | 2.37 |
| | sem | 5.84 | 22.84 | | | 4.71 | 1.71 |
| | non injected muscle | 0 | 0 | | | | |
| | non injected muscle | 0 | 0 | | | | |
| | mean | 0 | 0 | | | | |
| | sem | 0 | 0 | | | | |

A good correlation in human INF-β levels is found between the injected muscles and the corresponding sera.

Example 2

Gene Therapy of an EAE Mouse Model Using Intramuscular Administration of a Mouse INF-β Plasmid Construction of a MouseIFN-β Plasmid The mouse INF-β coding sequence of the cDNA (Higashi et al., 1983, The Journal of Biological Chemistry, 258, 9522–9529) shares homologies of 63% at the nucleotide and 48% at the amino acid level with respect to human INF-β cDNA (Tanigushi et al., 1980, supra). The first 21 amino acids are considered to be the signal sequence. It was obtained from a plasmid pMβ3 (mouse IFN-β cDNA inserted in a pBR322 plasmid; Higashi et al. 1983 supra).

The plasmid constructed, named pTG13114, is identical to the vector described in Example 1, with the only difference being here the mouse IFN-β cDNA.

In vitro Validation of pTG13114

The pCMV-mouse INF-β plasmid was assessed using a similar approach as described in Example 1, on calcium phosphate transfected C2C12 cells. The amount of mouse INF-β released in the culture media was measured on a regular basis up to 6 days after transfection with pTG13114. Fifteen microgram of plasmid were transfected in 6 well-plates seeded with $10^5$ cells/well cultured in Dulbecco's Modified eagle Medium (DMEM) containing 10% fetal calf serum.

The amount of mouse INF-β produced was measured using a CPE test, using mouse fibroblast 3T3 cells cultured in DMEM+10% FCS in 96-well plates and infected with VSV (M.O.I.=0.3). Cell viability was assessed 48 hrs after infection.

TABLE III mouse INF-β levels of culture supernatants after transfection or transduction

| Vectors | time after transfection/ transduction | IFN-β (IU/ml) |
|---|---|---|
| Plasmid pTG 13114 | 24 h | $4.5 \times 10^5$ |
| | 48 h | $2.2 \times 10^5$ |
| | 96 h | $5.6 \times 10^4$ |
| Control | 24 h | not deteced |

The table shows that high mouse INF-β expression was obtained following in vitro transfection. According to the CPE assay, the protein produced is biologically active.

Gene Therapy of EAE

Experimental Autoimmune Encephalomyelitis (EAE) in mice and rats has clinical and immunological similarities to the human disease and has therefore served as the prime experimental surrogate for multiple sclerosis. It can be induced by the injection of one of the major myelin constituants myelin basic protein (MBP) or proteolipid (PLP), or peptides of those components, emulsified in Complete Freund Adjuvant (CFA) and killed *Mycobacterium tuberculosis*.

The major pathologic feature of acute EAE has been shown to be perivascular inflammation associated with limited demyelination. Acute EAE is analogous to an exacerbation of multiple sclerosis and allows studies of the mechanisms responsible of the emergence of clinical signs as well as of potential treatments of multiple sclerosis.

Clinical signs observed in animals are generally assessed by establishing a scale ranging from 0 to 6:0=no weakness, 1=weakness of distal part of tail, 2=paralysis of the whole tail, 2=mild paralysis of one or both hind limbs, 3=moderate paraparesis or severe ataxia, 4=severe paraparesis, 5=total flaccid paraplegia with incontinence, and 6=moribond state.

One of the characteristic features of EAE is progressive weight loss during the clinical phase of the disease, which is rapidly reversed when the animals recover. In general, there is a good correlation between disease severity and magnitude of weight reduction.

We chose our EAE animal model from published data showing that the animals responded to recombinant INF-β (Yu et al., 1996, J. Neuroimmunol. 64, 90–100).

Induction of EAE

A total of 6 female SJL (H-$2^s$) mice (IFFA CREDO, France) aged>8 weeks were injected subcutaneously with PLP 139–151 peptide. The antigen was dissolved in acetic acid 10% then in water (50/50). The peptide solution was emulsified with CFA added with 4 mg/ml Mycobacterium tuberculosis (H37Ra) (final peptide concentration: 0.5 mg/ml).

A solution of Pertussis toxin (1 µg/ml PBS 0.15M pH 7.2) was injected intravenously (300 µl) at day 0 and 3 following immunization.

Clinical Observation: mice were assessed daily for both body weight and clinical signs using the following scale: 0=no weakness; 0.5=weakness of the distal part of tail only; 1=paralysis of the whole tail; 2=mild praparesis of one or both hind limbs; 3=moderate paraparesis or severe ataxia; 4=severe paraparesis; 5=total flaccid paraplegia with incontinence; 6=moribund state.

pCMV-IFN-β Treatment

A group of 3 mice received intramuscular injections of pTG13114 (pCMV-mouse IFN-β) prepared in NaCl 0.9% solution added with 1 mM (final) MgCl$_2$, in both right and left Tibialis anterior and quadriceps muscles (with 30 μg and 60 μg plasmid respectively). At day 4, the injected mice were treated with 3 ng/25 μl notexin. At day 7, the mice received a new series of plasmid injections as described above. The remaining 3 mice were not treated with pTG13114.

Figure 3:
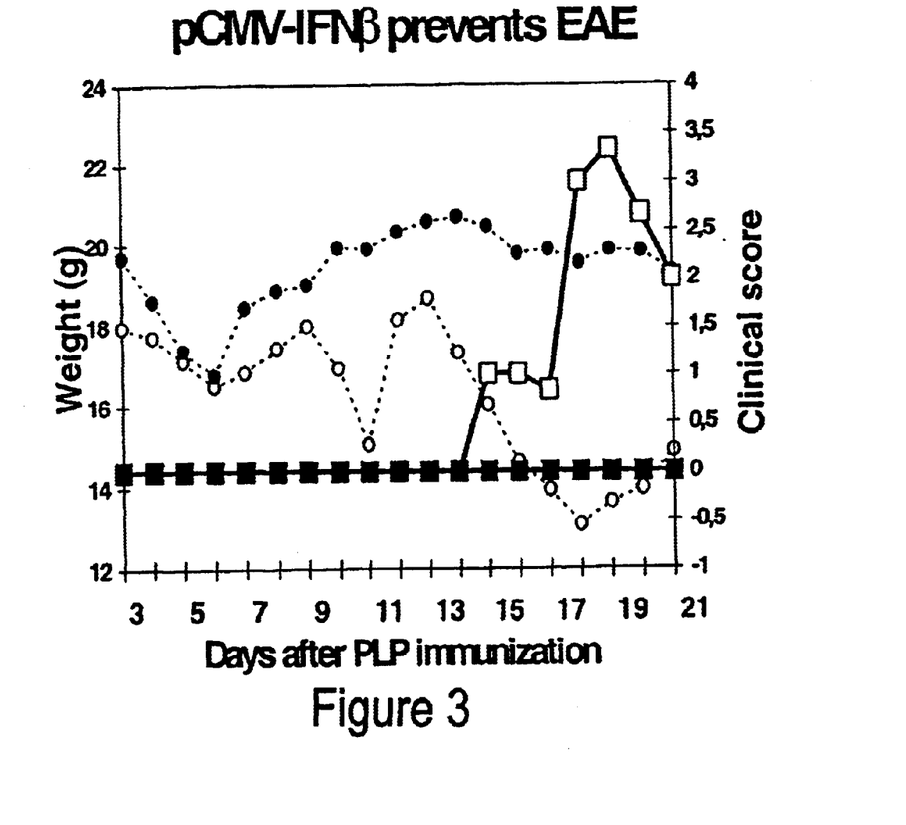
FIG. 3: Treatment with a mouse INF-β plasmid prevents clinical signs of EAE. Data points are mean values of 3 measurements. Full line/scares: clinical scores; dotted line/ circles: body weight. Full signs: mice treated with pTG13114. Empty signs: mice not treated with pTG13114.

Results are shown in FIG. 3. Mice treated with pTG13114 did not show any sign of EAE. The initial drop of body weight is most probably the consequence of the pertussis toxin intoxication. There is no other weight loss seen in this group of mice, whereas the typical weight loss was seen in the EAE mice which had not been treated with pTG13114.

Figure 4:
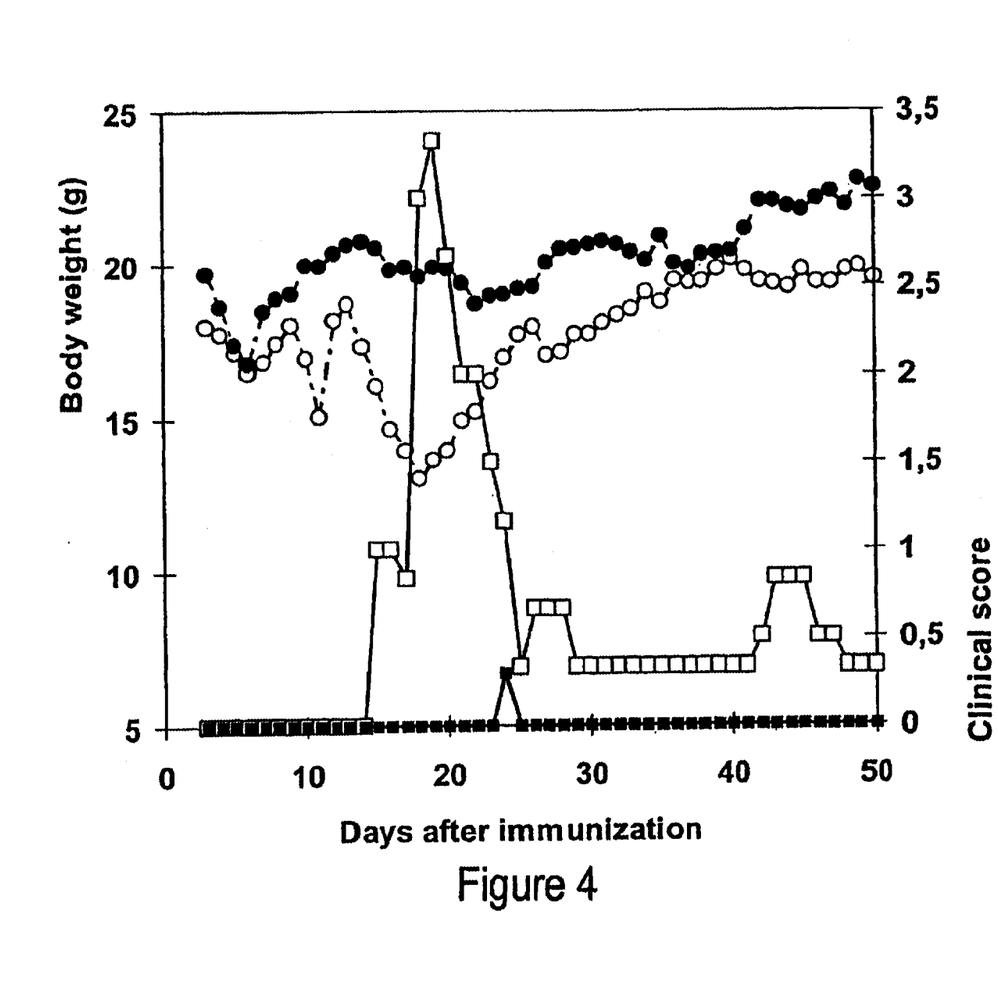
FIG. 4: Treatment with a mouse IFN-β plasmid prevents clinical signs of EAE. Results are measured during 50 days. Squares: clinical scores; circles: body weight. Empty labels: non-treated immunized mice. Full black labels: pCMV-mouse IFN-beta plasmid treated immunized mice. Data are mean values of 3 mice per group, recorded on a daily basis.

Treated animals were followed up to 50 days after immunization. Data are presented in FIG. 4 and show that no clinical signs of paralysis were seen in the mouse IFN-beta plasmid treated animals, whereas the non-treated immunized mice displayed 2 well characterized (clinical scores and body weight) relapses.

Example 3

Gene treatment of EAE (i) Induction of EAE has been done as described in Example 2.

Female SJL (H-$2^s$) mice (IFFA CREDO, France) aged>8 weeks were injected subcutaneously with PLP 139–151 peptide. The antigen was dissolved in acetic acid 10% than in water (50/50). The peptide solution was emulsified with CFA added with 4 mg/ml Mycobacterium tuberculosis (H37Ra) (final peptide concentration: 0.5 mg/ml).

A solution of Pertussis toxin (1 microg/ml PBS 0.15M pH 7.2) was injected intravenously (300 microl) at day 0 and 3 following immunization.

(ii) Treatment with plasmids

Five days before immunization, the mice received intramuscular injections of 3 ng/25 μl of notexin into both the right and left Tibialis anterior and quadriceps muscles. Treatment consisted in 2 consecutive injections (48 hrs and 24 hrs prior to immunization, respectively) of 75 μg/30 μl and 125 μg/50 μl of either pTG13114 (pCMV-mouse IFN beta) or pTG11022 (empty plasmid) prepared in NaCl 0.9% solution added with 1 mM (final) $MgCl_2$, in right+left Tibialis anterior and quadriceps muscles, respectively.

The mice were divided into 3 groups:

control EAE mice (immunized, not injected with plasmid) (6 mice)

Plasmid-IFN (immunized, treated with pTG13114) (5 mice)

empty plasmid (immunized, treated with pTG11022) (6 mice)

Parameters were body weight and cumulated clinical scores (addition of the clinical scores recorded daily per mouse).

Figure 5:
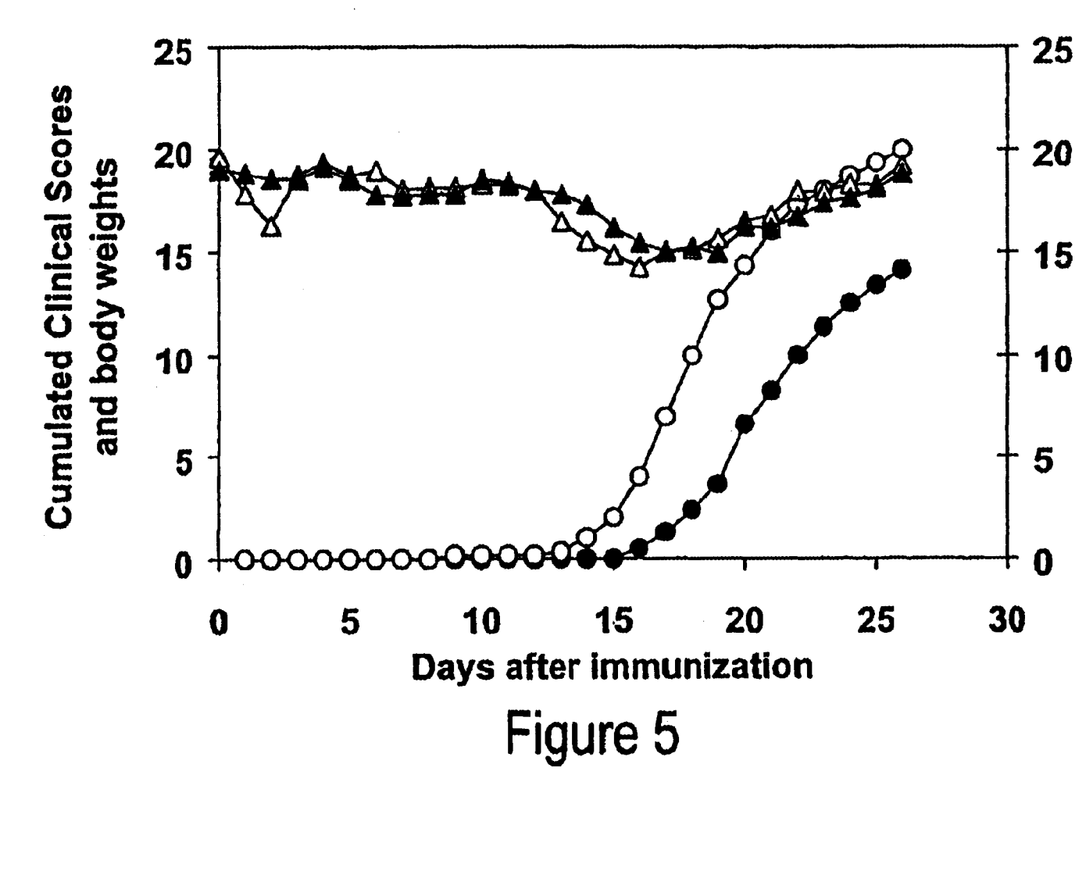
FIG. 5: Treatment with pCMV-mouse IFN beta protects against EAE. Circles: cumulated clinical scores; Triangles: Body weights. Empty labels: control. Full black labels: plasmid-mouse IFN-beta (pTG13314) treated mice. Data are mean values of 3 (control mice) or 4 determinations (pTG13114 treated mice).

As shown by FIG. 5, in the conditions described, the mice treated with plasmid-IFN (pTG13114) showed reduced signs and slight delay of onset of EAE. 5 out of 6 mice of the empty-plasmid group probably due to the disease, as they died all after day 9 following immunization. When early death occurs, this is related to the heavy immunization procedure (especially pertussis toxin intoxication, used to open the brain-blood barrier). In the control EAE group, 3 mice died, whereas only 1 mouse died in the plasmid-IFN treated group, suggesting a beneficial impact of the treatment with plasmid-IFN.

The mice treated with pTG13114 displayed a much better shape than the 2 other groups: nice shiny fur in the pTG13114-treated group versus hirsute fur (indicative of an abnormal diseased condition) in the 2 other groups (non-treated and empty plasmid groups).

In this example, the effect on the body weight was moderate.

What is claimed is:

1. A method for the treatment of multiple sclerosis comprising administering directly to the muscle cells of a patient in need of such treatment an effective amount of naked DNA comprising a nucleic acid encoding beta-interferon which comprises a beta-interferon secretory signal, wherein said naked DNA is suitable for administration by injection.

2. The method of claim 1, wherein said beta-interferon is human beta-interferon.

3. The method of claim 1, wherein said naked DNA further comprises a promoter element selected from the group consisting of viral promoters and muscle specific promoters.

4. The method of claim 1, wherein said naked DNA further comprises at least one enhancer element.

5. The method of claim 1, wherein said naked DNA further comprises at least one sequence ensuring the polyadenylation of the transcribed RNA molecules.

6. The method of claim 1, wherein said effective amount is from about 1 μg to 1 g.

7. The method of claim 1, wherein said naked DNA is in a pharmaceutically acceptable carrier.

8. The method of claim 7, wherein said pharmaceutically acceptable carrier is a solution.

9. A method for the treatment of multiple sclerosis comprising administering directly to the muscle cells of a patient in need of such treatment an effective amount of naked DNA comprising a nucleic acid encoding human beta-interferon which comprises a beta-interferon secretory signal, wherein said naked DNA is suitable for administration by injection.

* * * * *

SEQUENCE LISTING

<160> NUMBER OF SEQ ID NOS: 3

<210> SEQ ID NO 1
<211> LENGTH: 187
<212> TYPE: PRT
<213> ORGANISM: Homo sapiens

<400> SEQUENCE: 1

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

-continued

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
        130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
            180                 185

<210> SEQ ID NO 2
<211> LENGTH: 166
<212> TYPE: PRT
<213> ORGANISM: Homo sapiens

<400> SEQUENCE: 2

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Gly Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 3
<211> LENGTH: 564
<212> TYPE: DNA
<213> ORGANISM: Homo sapiens

<400> SEQUENCE: 3
atgaccaaca agtgtctcct ccaaattgct ctcctgttgt gcttctccac tacagctctt     60
tccatgagct acaacttgct tggattccta caaagaagca gcaattttca gtgtcagaag    120
ctcctgtggc aattgaatgg gaggcttgaa tattgcctca aggacaggat gaactttgac    180
atccctgagg agattaagca gctgcagcag ttccagaagg aggacgccgc attgaccatc    240
tatgagatgc tccagaacat ctttgctatt ttcagacaag attcatctag cactggctgg    300
aatgagacta ttgttgagaa cctcctggct aatgtctatc atcagataaa ccatctgaag    360
acagtcctgg aagaaaaact ggagaaagaa gatttcacca ggggaaaact catgagcagt    420

```
                                                -continued ctgcacctga aaagatatta tgggaggatt ctgcattacc tgaaggccaa ggagtacagt    480
cactgtgcct ggaccatagt cagagtggaa atcctaagga acttttactt cattaacaga   540
cttacacgtt acctccgaaa ctga                                          564
```